United States Patent
Hall (12)

(10) Patent No.: US 6,475,172 B1
(45) Date of Patent: Nov. 5, 2002

(54) INSTRUMENT FOR CLEANING TONSILS

(76) Inventor: Barbara J. Hall, 9234 Vermilion Rd., Amherst, OH (US) 44001

( * ) Notice: Subject to any disclaimer, the term of this patent is extended or adjusted under 35 U.S.C. 154(b) by 0 days.

(21) Appl. No.: 09/652,294

(22) Filed: Aug. 31, 2000

(51) Int. Cl.$^7$ ............................................... A61H 13/00
(52) U.S. Cl. ....................... 601/137; 606/161; 601/139
(58) Field of Search .................... 606/161; 601/136, 601/137, 139, 141; 15/110, 111; 433/143, 141

(56) References Cited

U.S. PATENT DOCUMENTS

| | | | |
|---|---|---|---|
| 319,454 A | | 6/1885 | Cochrane |
| 1,541,664 A | | 6/1925 | Schultes |
| 1,701,616 A | * | 2/1929 | Gross |
| 2,424,767 A | | 7/1947 | Moses |
| 2,651,068 A | * | 9/1953 | Seko ........................... 015/111 |
| D212,868 S | | 12/1968 | Olson et al. |
| 3,890,964 A | * | 6/1975 | Castanedo ................. 128/62 R |
| 4,044,770 A | * | 8/1977 | Ocel et al. .................. 128/304 |
| 4,345,599 A | | 8/1982 | McCarrell |
| 4,488,327 A | * | 12/1984 | Snider .......................... 015/111 |
| 4,732,150 A | | 3/1988 | Keener, Jr. |
| 5,201,741 A | | 4/1993 | Dulebohn |
| 5,217,475 A | * | 6/1993 | Kuber .......................... 606/161 |
| 5,230,356 A | * | 7/1993 | Villas .......................... 132/329 |
| 5,352,219 A | | 10/1994 | Reddy |
| D381,426 S | | 7/1997 | Koros et al. |
| 5,709,004 A | | 1/1998 | Paduano et al. |
| D390,659 S | | 2/1998 | Chan et al. |
| 5,779,475 A | * | 7/1998 | Patel ........................... 433/141 |
| 5,868,769 A | * | 2/1999 | Rosenblood ................. 606/161 |
| 5,893,860 A | * | 4/1999 | Ripich et al. ............... 606/161 |
| 5,915,433 A | * | 6/1999 | Hybler ........................ 015/111 |
| D414,866 S | | 10/1999 | Szabo |
| 6,013,089 A | * | 1/2000 | Goldberg ..................... 606/161 |
| 6,015,415 A | | 1/2000 | Avellanet |
| 6,056,763 A | * | 5/2000 | Parsons ....................... 606/161 |

FOREIGN PATENT DOCUMENTS

| | | |
|---|---|---|
| DE | 39 08 113 | 9/1990 |
| SU | 1676602 | 9/1991 |
| SU | 1697766 | 12/1991 |

\* cited by examiner

Primary Examiner—Justine R. Yu

(57) ABSTRACT

A tonsil cleansing tool for removing a spot of debris and build up from a tonsillar pit on a tonsil comprises an elongate shaft having a loop shaped element attached to one end and a presser element having an opening therethrough attached to the other end. The method of using the tonsil cleaning tool includes: identifying the spot of debris and build up on the tonsil; applying pressure to a surface of the tonsil in close proximity to the spot for dislodging the debris and build up from the tonsillar pit; and removing the debris or build up from the surface of the tonsil.

9 Claims, 2 Drawing Sheets

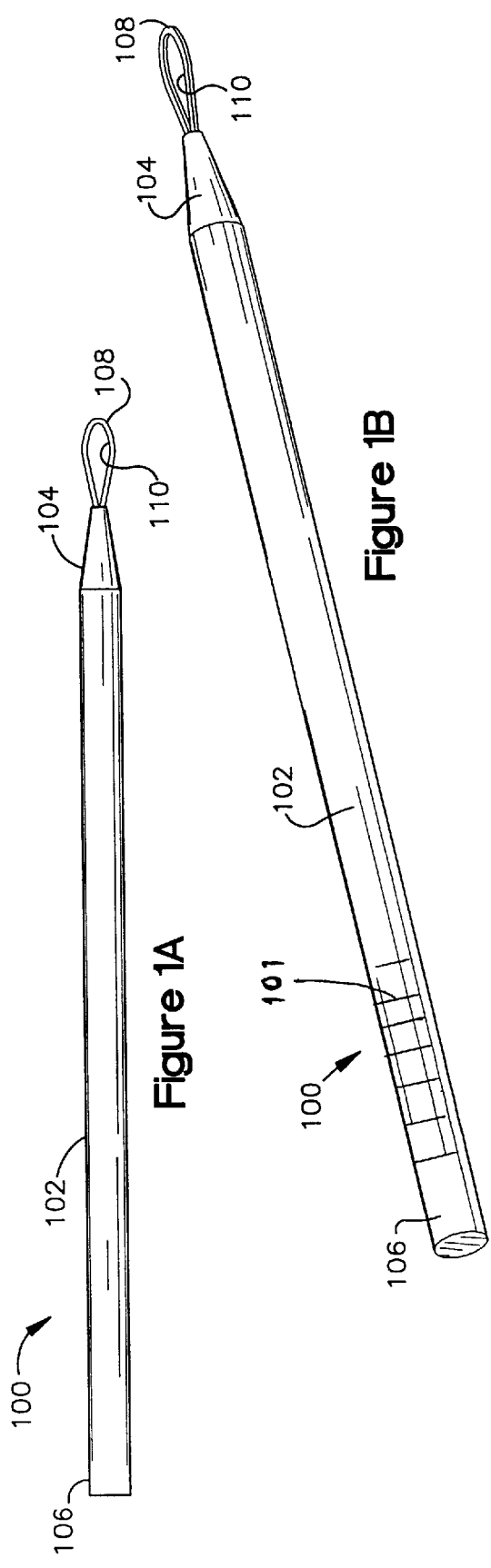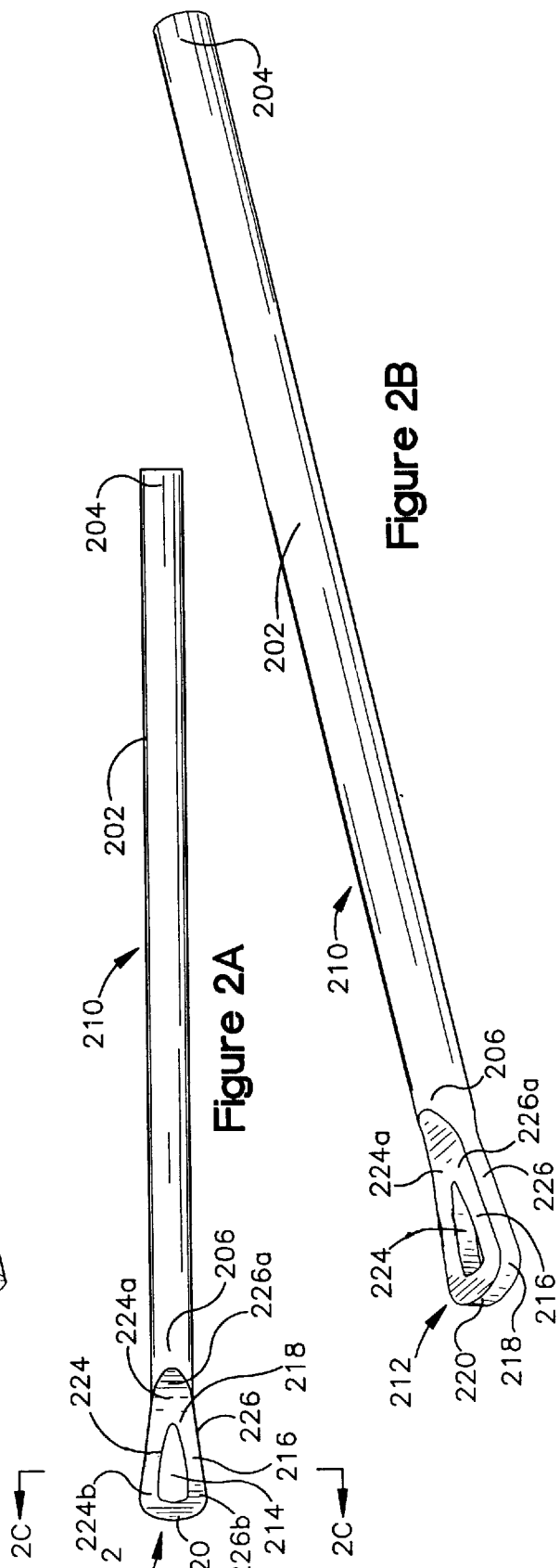

INSTRUMENT FOR CLEANING TONSILS

TECHNICAL FIELD OF THE INVENTION

The present invention is directed to the field of mouth hygiene and more particularly to an instrument for dislodging and removing debris and other tonsil build-up that collects on the tonsils.

BACKGROUND OF THE INVENTION

Human tonsils are small collections of lymphoid tissue located in the pharynx. At the entrance to the pharynx and on each side of the tongue are the two palatine tonsils. On the back of the tongue is the lingual tonsil. On the back of the pharynx are the pharyngeal tonsils, which are also known as the adenoids. Together these collections of lymphoid tissue form a ring within the pharynx that protects the entrance to the throat. One of the primary functions of tonsils is to trap bacteria that enter the throat thereby protecting the body from assault by pathogenic microorganisms.

Human tonsils are generally almond shaped and have small "pits" or cavities in them which primarily function to collect invading microorganisms. However, in addition to their primary function, these small pits can also collect small food particles and sinus drainage. This build-up of bacteria, food particles, and other debris generally appears as white or yellow spots on the tonsil and very often emits a foul odor causing bad breath.

Bad breath, or halitosis, can be very embarrassing for the person suffering from it. There are many remedies available in the marketplace for addressing bad breath. Indeed there is an entire industry dedicated to dealing with this problem. Such remedies include mouthwashes, breath mints and other candies, breath-freshening sprays, and breath-freshening gums. While these remedies may mask the foul odor in the afflicted person's breath, the relief is often temporary. Thus, there is a continuing need for remedies for bad breath that offer the afflicted person longer lasting relief.

An attempt to address the problem of halitosis is disclosed in U.S. Pat. No. 5,709,004 ('004) to Paduano et al. which is directed to a the toothbrush. The toothbrush of the '004 patent is comprised of two longitudinal handle sections that separate and form a scraper device that enables the user to scrape the tongue. The scraper device removes food residues, bacterial coatings, and nicotine residues from the surface of the tongue which may contribute to bad breath. However, this device fails to address bad breath associated with tonsillar build up.

In addition, there are many devices known in the art for ensnaring tonsils and other body parts. For example see: U.S. Pat. No. 1,541,664 to Schultes; U.S. Pat. No. 4,345,599 to McCarrell; U.S. Pat. No. 4,732,150 to Keener; U.S. Pat. No. 5,201,741 to Dulebohn; U.S. Pat. No. 5,352,219 to Reddy; and U.S. Pat. No. 6,015,415 to Avellanet. The devices described in the previously mentioned patents generally have a loop end that is used to capture within its opening the tonsil or other body part. Then, while holding the tonsil or other body part within the loop, the surgeon can sever the tonsil or other body part from the body.

U.S. Pat. No. 2,424,767 to Moses and U.S. Pat. No. 319,454 to Cochrane describe veterinary instruments useful in removing food particles or other foreign objects from a choking animals throat.

None of the prior art, however, enables a user to remove the food particles and other debris that get trapped in the tonsils and contribute to bad breath. With the need for a remedy for bad breath caused by the build-up of bacteria, food particles, and other debris on tonsils, the present invention will be welcomed on our society.

BRIEF DESCRIPTION (SUMMARY) OF THE INVENTION

According to the invention, a tonsil cleansing tool is constructed of an elongate shaft having a first end and a second end opposite the first end, and a loop shaped element attached to the elongate shaft at the first end. The loop shaped element has an opening and extends longitudinally outward from the elongate shaft. The elongate shaft can be constructed of any suitable material such as a durable plastic or other moldable material, or metal. Preferably the elongate shaft is made of a moldable plastic that allows for easy gripping by the user and contributes to the ease of use. Additionally, the elongate shaft can be designed with surface ridges which run either longitudinally along the elongate shaft or circumferentially around the elongate shaft, or both. The elongate shaft and the loop shaped element may be formed as a unitary structure.

According to another aspect of the invention, the tonsil cleansing tool comprises an elongate shaft having a first end and a second end opposite the first end, and a presser element having an opening therethrough and a rearwardly disposed presser bar. The presser element is attached to the second end of the elongate shaft. The presser element may further comprise a plurality of arms. Each of the arms has a first end and second end opposite the first end. The first end of each arm is attached to the second end of the elongate shaft and the second end of each arm is attached to the presser bar. The arms extend longitudinally outward from the elongate shaft. Preferably, the presser element is triangular in shape and the opening therein is triangular in shape. The elongate shaft and the presser element may be formed as a unitary structure.

According to another aspect of the invention, the tonsil cleansing tool comprises an elongate shaft having a first end and a second end opposite the first end; a loop shaped element having an opening and extending longitudinally outward from the elongate shaft; and a presser element having an opening and a rearwardly disposed presser bar. The loop shaped element is attached to the first end of the elongate shaft and the presser element is attached to the second end of the elongate shaft. The presser element can be constructed of at least one and preferably a plurality of arms. Each arm has a first end and second end opposite the first end. The first end of the arm is attached to the elongate shaft and the second end of the arm is attached to the presser bar. The arm extends longitudinally outward from the elongate shaft. Preferably the presser element is triangular in shape and the opening therein is triangular in shape. The elongate shaft and the presser element may be formed as a unitary structure. Preferably the presser element is formed of a moldable plastic and the loop shaped element is formed of metal. Preferably the elongate shaft is formed in shape selected from the group comprising: round, pentagonal, hexagonal, and octagonal. The elongate shaft may further comprise surface ridges that run circumferentially or longitudinally along the over surface of the elongate shaft.

According to another aspect of the invention, the method for cleaning debris and build up from a tonsillar pit or cavity comprises the steps of: (a) identifying a spot of debris and build up on or within a pit or cavity opening to the surface of the tonsil; (b) applying pressure to the surface of the tonsil in close proximity to the spot of debris and build up thereby dislodging the debris and build up from the tonsillar pit; and (c) removing the debris or build up from the surface of the tonsil.

Other aspects, features and advantages of the invention will become apparent in light of the following description thereof.

BRIEF DESCRIPTION OF THE DRAWINGS

Reference will be made in detail to preferred embodiments of the invention, examples of which are illustrated in the accompanying drawings. The drawings are intended to be illustrative, not limiting. Certain elements in selected ones of the drawings may be illustrated not-to-scale, for illustrative clarity.

Often, similar elements throughout the drawings may be referred to by similar references numerals. For example, the element 199 in a figure (or embodiment) may be similar in many respects to the element 299 in an other figure (or embodiment). Such a relationship, if any, between similar elements in different figures or embodiments will become apparent throughout the specification, including, if applicable, in the claims and abstract. In some cases, similar elements may be referred to with similar numbers in a single drawing. For example, a plurality of elements 199 may be referred to as 199a, 199b, 199c, etc.

Figure 5:
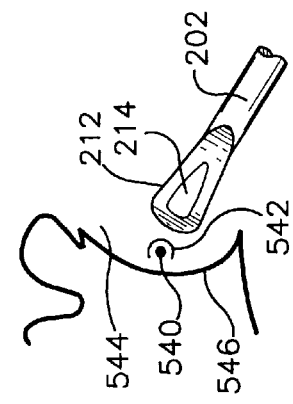
Figure 4:
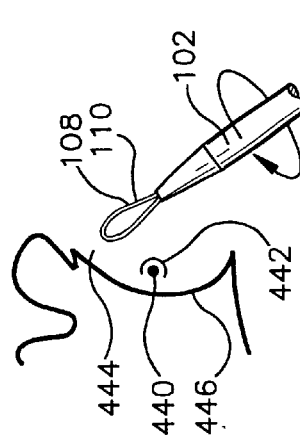
Figure 2C:
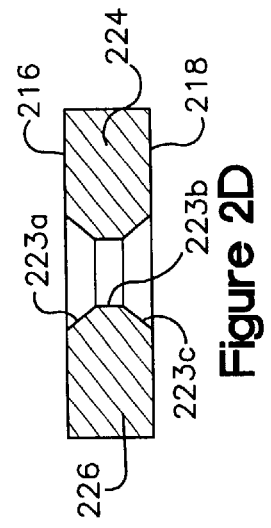
Figure 2D:
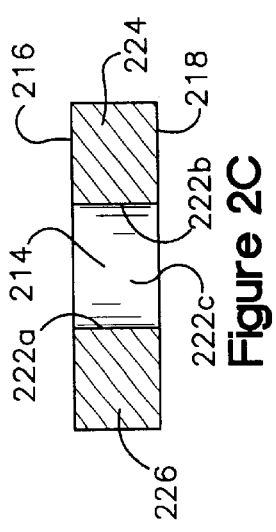
Figure 3A:
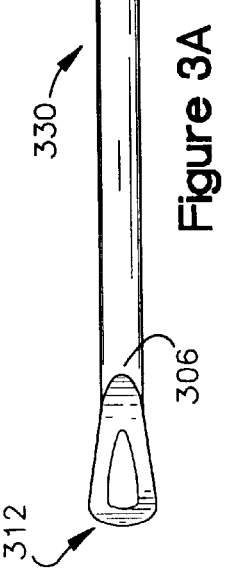
Figure 3B:
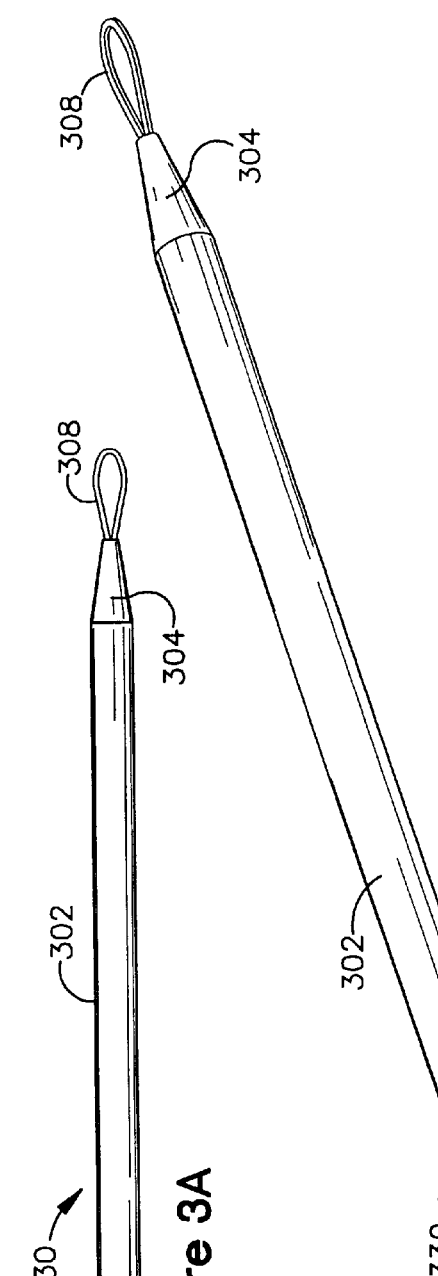

The structure, operation, and advantages of the present preferred embodiment of the invention will become further apparent upon consideration of the following description taken in conjunction with the accompanying drawings, wherein:

FIG. 1A is a side perspective view of a first embodiment of a tonsil cleansing tool according to the invention;

FIG. 1B is a top perspective view of the first embodiment of the tonsil cleansing tool of FIG. 1A according to the invention;

FIG. 2A is a side perspective view of a second embodiment of a tonsil cleansing tool according to the invention;

FIG. 2B is a perspective view of the second embodiment of the tonsil cleansing tool of FIG. 2A according to the invention;

FIG. 2C is a view through 2C—2C of FIG. 2A;

FIG. 2D is an alternative embodiment of the opening through presser element of the tonsil cleansing tool of FIG. 2A;

FIG. 3A is a side perspective view of a third embodiment of a tonsil cleansing tool according to the invention;

FIG. 3B is a top perspective view of the third embodiment of the tonsil cleansing tool of FIG. 3A according to the invention;

FIG. 4 is a partial front view of a tonsil illustrating one use of the first embodiment of the tonsil cleansing tool according to the invention; and FIG. 5 is a partial front view of a tonsil illustrating one use of the second embodiment of the tonsil cleansing tool according to the invention.

DETAILED DESCRIPTION OF THE INVENTION

First Embodiment

FIGS. 1A and 1B, being side and top perspective views, respectively, illustrate a first embodiment of a tonsil cleansing tool 100 according to the present invention. The tonsil cleansing tool 100 comprises an elongate shaft 102 having a first end 104 and a second end 106. The elongate shaft 102 is generally in the form of a rod or tube and can be formed in any desired shape, such as for example, round, pentagonal, hexagonal or octagonal in shape. Preferably, the elongate shaft 102 is formed in a shape that allows for easy gripping and handling by the user.

The elongate shaft 102 may be constructed of any suitable material such as a durable plastic, metal or other moldable material. Preferably, the elongate shaft 102 is made of a moldable plastic that allows for easy gripping by the user and contributes to the ease of use. Further to that end, the elongate shaft 102 can be designed with surface ridges (not shown) which run either longitudinally along the elongate shaft 102 or circumferentially around the elongate shaft 102, or both.

In the first embodiment shown in FIGS. 1A and 1B, a loop shaped element 108 is attached to the elongate shaft 102 at the first end 104 and extends longitudinally outward therefrom. The loop shaped element 108 defines an opening 110 projecting outward from the first end 104. The loop shaped element 108 can be attached to the elongate shaft 102 in any suitable manner. Preferably the loop shaped element 108 is inserted or attached within a cavity or bore in the first end 104 of the elongate shaft 102 so as not to risk injury to the user. The elongate shaft 102 and the loop shaped element 108 can be formed as a unitary structure. Preferably the elongate shaft 102 is tapered at the first end 104, as depicted in FIG. 1A, further contributing to the ease of use.

The loop shaped element 108 may be constructed of any suitable stiff material, such as a durable plastic or other moldable plastic, metal, or coated wire, that will allow the loop shaped element 108 to retain its shape. The cross section of the loop shaped element is illustrated as being rectangular, but can be circular, oval, square, hexagonal, or of any other desired shape suitable for drawing across the surface of a tonsil to remove any accumulation of debris or food that is caught within the pits or cavities formed extending from the surface into the tonsil.

Second Embodiment

Referring to FIGS. 2A and 2B, in side and perspective view respectively, there is illustrated a second embodiment of a tonsil cleansing tool 210 of the present invention. The tonsil cleansing tool 210 includes an elongate shaft 202 (compare 102) having a first end 204 (compare 104) and a second end 206 (compare 106). A presser element 212 is attached to the second end 206 of the elongate shaft 202. The presser element 212 is generally flat and has an opening 214 extending through the flattened upper and lower surfaces 216, 218. The outward end of the presser element 212 forms a rearwardly disposed presser bar 220. While the opening 214 is preferably triangular in shape, it is within the terms of the present invention to form the opening of any desired shape such as square, rectangular, oval or round. The surfaces 222a, 222b, 222c that define the perimeter of the opening 214, as shown in FIG. 2C, are preferably disposed parallel to each other so that the opening 214 in the upper surface 216 is substantially the same as the opening 214 in the lower surface 218. In an alternative embodiment, as shown in FIG. 2D, the surfaces 223a, 223b, and 223c that define the perimeter of the opening 214, have wall surfaces 223a and 223b adjoined at their inner end to parallel wall surfaces 223b in the central section of the opening 214 through presser element 212. The outer ends of the wall surfaces 223a and 223b flare outward from their inner ends at an angle so that the opening 214 in the upper surface 216 and the opening in the lower surface 218 are larger than the size of the opening in the central section. This funnel shape from either surface of the presser element enables the presser element to be used from either side. The opening will hold the debris so that it can be seen by the user. The design will also funnel debris to the center of the hole for easy removal. The rearward presser element 212, in the preferred embodiment of the invention, can be constructed of two support arms 224, 226 extending longitudinally outward from the second end 206 of the elongate shaft 102. The two support arms 224, 226 each having a first end 224a, 226a secured to the second end 206 of the elongate shaft 102 and a second end 224b, 226b opposite from the first end and secured to opposite ends of the presser bar 220. As depicted in FIGS. 2A and 2B, the presser bar 220 is disposed essentially perpendicular to the elongate shaft 202. Alternatively, the presser bar 220 can be disposed in an angular relationship (not shown), other than perpendicular, to the elongate shaft 202.

The presser element 212 may be constructed of any suitable material such as a durable plastic, metal, or other moldable material. Preferably the presser element 212 is made of a moldable plastic and formed as a unitary structure with the shaft 202.

Third Embodiment

Referring to FIGS. 3A and 3B, there is illustrate a preferred embodiment of the tonsil cleansing tool 330 of the present invention which incorporates the features of the first embodiment shown in FIGS. 1A and 2A and the second embodiment shown in FIGS. 2A, 2B, and 2C. The tonsil cleansing tool 330 comprises the elongate shaft 302 (compare 102, 202) with the loop shaped element 308 (compare 108) affixed to the first end 304 (compare 104) of shaft 330 and the presser element 312 (compare 212) secured to the second end 306 (compare 106). In a preferred embodiment of the invention, the loop shaped element 308, the presser element 312, and the elongate shaft 302 are formed as a unitary structure.

METHOD OF USING

The tonsil cleansing tools 100, 210, 330 of the present invention can be used to remove debris and other build-up that accumulates in tonsillar pits and cavities thereby eliminating bad breath.

Referring to FIG. 4, there is illustrated one method of using an embodiment of the present invention. That is, the loop shaped element 108, 308 of the tonsil cleansing tools 100, 330 can be used to remove debris 440 lodged in a tonsillar pit 442 and extending above the surface 444 of the tonsil 446. The loop shaped element 108 can be placed over the debris 440 such that the debris 440 becomes wedged in the opening 110 of the loop shaped element 108. The user then rotates the tonsil cleansing tool 100 in either a clockwise (as depicted in FIG. 4) or counterclockwise manner thereby dislodging the debris 440. Additionally, the loop shaped element 108 can be passed across the debris 440 by the user in a "wiping motion" such that the debris 440 is captured within the opening 110 and becomes dislodged. Once captured in the opening 110, the dislodged debris 440 will generally remain in the opening 110 and can then be removed from the subject's mouth for disposal.

FIG. 5 illustrates another method of using an embodiment of the present invention. That is, the presser element 212 can be used to remove debris 540 or other build up lodged in a tonsillar pit 542. The user must first identify a tonsillar pit 542 containing debris 540 (which appears as a spot on the tonsil 546). The rearward presser bar 220 is then placed against the surface 544 of the tonsil 546 next to the tonsillar pit 542 containing debris 540. The user then gently presses the presser element 212 against the tonsil 546. The pressing creates pressure within the tonsil 546 that causes the debris 540 to become dislodged. Once dislodged, the user can pass the presser end 212 across the debris 540 in a "wiping motion" such that the debris is captured in the opening 214 of the presser element 212 and can be removed from the subject's mouth.

In another embodiment, the present invention is directed to a method for cleaning debris and build up from a tonsillar pit disposed on a tonsil. The method comprises the following steps: a. identifying a spot of debris or buildup on the tonsil; b. applying pressure to the surface of the tonsil in close proximity to the spot thereby dislodging the debris and build up from the tonsillar pit; and c. removing the debris or build up from the surface of the tonsil.

Preferably the tonsil cleansing tool of the present invention is used on a regular basis, such as once a day or every other day. Additionally, the user should thoroughly rinse his/her mouth with water after each use. The tonsil cleansing tool should be washed with soap or other suitable cleanser and rinsed after each use. Preferably the tonsil cleansing tool is not to be shared among more than one subject since germs may be transmitted between subjects.

While the elongate shafts 102, 202, 302 are shown to be of a single piece construction, it is within the terms of the present invention to form the shafts of two sections that can screw together, fold and lock into position or telescope into each other and lock into place when extended. Further, the elongate shafts 102, 202, 302 can have a soft rubber coating which is either smooth or with ridges for easy gripping of the tonsil tool.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

What is claimed is:

1. A tonsil cleansing tool for cleaning debris and build up from a tonsillar pit or cavity of a tonsil comprising:

an elongate shaft having a first end and a second end opposite said first end;

a loop shaped element having a first opening attached to the elongate shaft at the first end and extending longitudinally away from the elongate shaft wherein a smallest dimension of the first opening being at a point where the loop shaped element is attached to the shaft, the first opening of the loop shaped element being sized and shaped specifically for cleaning debris and build up from the tonsillar pit or cavity;

a presser element having a second opening therethrough and a rearward presser bar at one end, said presser element being attached to the second end of the elongate shaft and having a lower surface and an upper surface with the second opening extending through the presser element from the upper surface to the lower surface;

the presser bar having a thickness less than said elongate shaft, the presser bar being sized for pressing against the tonsil and capturing debris and build up from the tonsillar pit or cavity with the second opening extending through the presser element.

2. The tonsil cleansing tool according to claim 1 wherein the elongate shaft is formed of a moldable plastic.

3. The tonsil cleansing tool according to claim 1 wherein the presser element is formed of a moldable plastic and the loop shaped element is formed of a material selected from the group comprising moldable plastic and metal.

4. The tonsil cleansing tool according to claim 1 wherein the second opening of the presser element has a shape selected from the group comprising square, rectangular, oval and round shapes.

5. The tonsil cleansing tool according to claim 4 wherein the second opening of the presser element has sidewalls that are parallel to each other.

6. The tonsil cleansing tool according to claim 4 wherein the second opening of the presser element has sidewalls with two surfaces at an angle to each other so that a size of the second opening at each of the upper surface and the lower surface is larger than a size of the second opening in a central section of the presser element.

7. The tonsil cleansing tool according to claim 1 wherein the elongate shaft and the presser element are formed as a unitary structure.

8. The tonsil cleansing tool according to claim 7 wherein the elongate shaft is formed in shape selected from the group comprising round, pentagonal, hexagonal, and octagonal.

9. The tonsil cleansing tool according to claim 8 wherein the elongate shaft further comprises surface ridges.

* * * * *